United States Patent [19]

Sato

[11] Patent Number: 4,634,557

[45] Date of Patent: Jan. 6, 1987

[54] DEUTEROPORPHYRIN DERIVATIVE OR SALT THEREOF

[75] Inventor: Haruo Sato, Chiba, Japan

[73] Assignee: Sato Pharmaceutical Research Institute Ltd., Tokyo, Japan

[21] Appl. No.: 690,579

[22] Filed: Jan. 11, 1985

[30] Foreign Application Priority Data

Jan. 18, 1984 [JP] Japan .................................. 59-6745

[51] Int. Cl.$^4$ ........................................ C07D 487/22
[52] U.S. Cl. ........................................ 540/145; 424/9
[58] Field of Search .................................. 260/245.91

[56] References Cited

U.S. PATENT DOCUMENTS 3,004,985 10/1961 Obika et al. .................... 260/245.91

OTHER PUBLICATIONS

Dolphin, The Porphyrins, vol. 1, Academic Press, New York (1978), pp. 297-298.
Kessel et al., Porphyrin Photosensitization, Plenum Press, New York (1983), pp. 165-179.
Chemical Abstracts, vol. 97, No. 21, Nov. 22nd, 1982, p. 408, No. 177901y, "Some Patterns in the Transport . . .".
Chemical Abstracts, vol. 93, No. 3, Jul. 21st, 1980, p. 59, No. 19225u, "Toxic and Radioprotective Properties of . . .".

*Primary Examiner*—Richard L. Raymond
*Attorney, Agent, or Firm*—Oblon, Fisher, Spivak, McClelland, & Maier

[57] ABSTRACT

Disclosed herein is a deuteroporphyrin derivative represented by the following general formula:

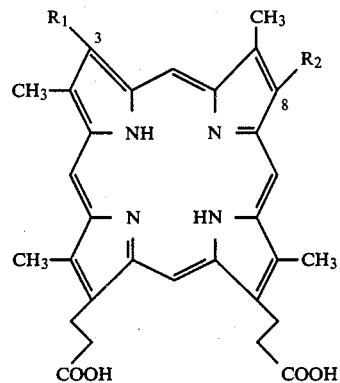

wherein one of $R_1$ and $R_2$ means —CH(CH$_3$)—OR, R being a lower alkyl group, and the other denotes —CH=CH$_2$, or $R_1$ and $R_2$ both mean —CH(CH$_3$)—OR, R having the same meaning as defined above, or a salt thereof. The deuteroporphyrin derivative or its salt can be readily obtained in its pure form and is useful as a photosensitizer in the laser irradiation therapy of cancers.

3 Claims, 1 Drawing Figure

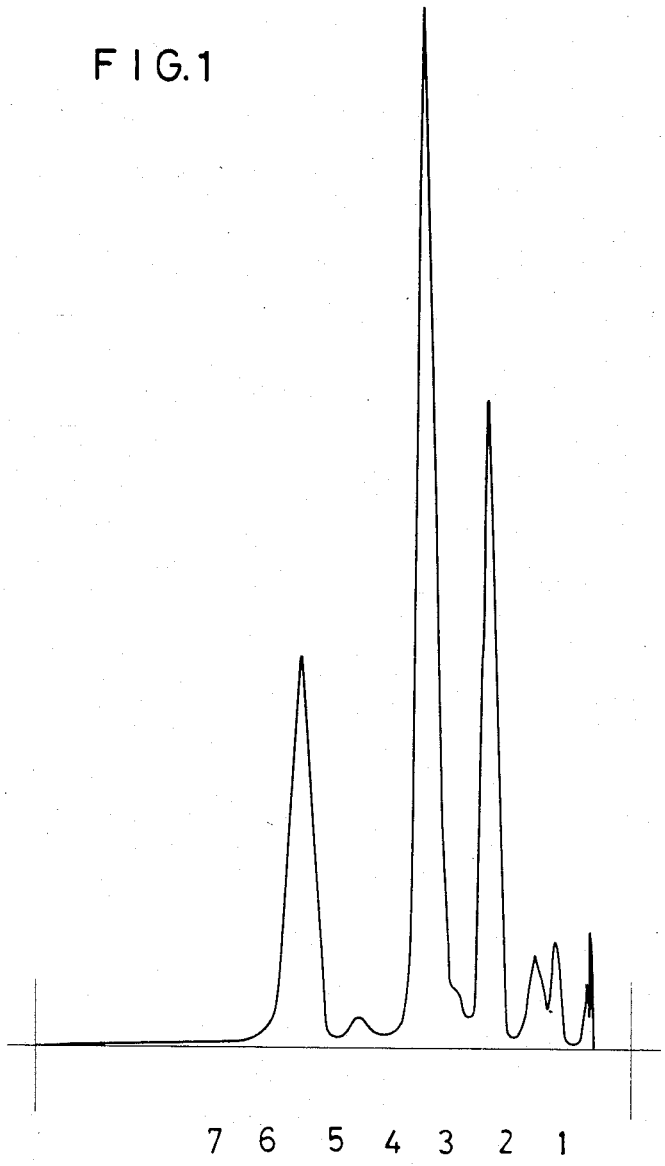

DEUTEROPORPHYRIN DERIVATIVE OR SALT THEREOF

This invention relates to a novel deuteroporphyrin derivative, and more specifically to a deuteroporphyrin derivative represented by the following general formula (I):

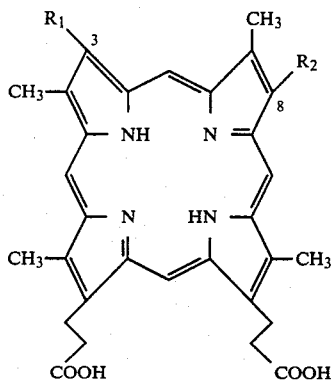

wherein one of $R_1$ and $R_2$ means —CH(CH$_3$)—OR, R being a lower alkyl group, and the other denotes —CH=CH$_2$, or $R_1$ and $R_2$ both mean —CH(CH$_3$)—OR, R having the same meaning as defined above, or a salt thereof.

Therapeutic application of laser is widely carried out in recent years. A significant advancement has been achieved particularly in its application for the treatment and diagnosis of cancers. Among such achievements, Dougherty et al. have obtained excellent results in the early-stage detection and treatment of cancers relying upon the combination of a hematoporphyrin derivative (HPD) and argon laser. Namely, a photosensitive substance having oncotropicity such as a hematoporphyrin derivative is in advance administered to have it accumulate in a tumor. Then, making use of the good penetration and linearlity of laser into vital tissues, laser is irradiated to make a diagnosis whether the tumor is present or not. In addition, the tumored site is selectively destructed using argon laser of low energy.

In ultraviolet therapy and radiotherapy, it has been practiced for many years to administer photosensitive substances and then to treat cancers as mentioned above. Coupled with the development of laser in recent years, attention has been centered on the development of substances which are sensitive to laser beams and have oncotropicity.

D. Kessel et al. investigated the oncotropicity and laser beam sensitivity on a variety of porphyrin compounds and provided hematoporphyrin. As indicated by Dolphin in his textbook "The Porphyrins", Vol. 1, Academic Press, PP 297-298 (1978); it is however difficult to obtain hematoporphyrin in its pure form. As a matter of fact, the HPD employed in the above-mentioned study by Dougherty et al. was a mixture of several kinds of substances analogous to hematoporphyrin. This has presented a considerable obstacle in conducting basic researches and also in using it for clinical applications.

Recently, many researches have been reported with respect to the isolation and structural determination of various components of HPD and the accumulation of such components in cancered cells [David Kesssel, Thomas J. Dougherty: "Porphyrin Photosensitization", P 165 (1983)]. In the above literature, hematoporphyrin (HP) is treated with sulfuric acid in acetic acid to obtain HPD. It has been reported that the majority of the thus-obtained product is made up of acetylated derivatives, among which the principal one is 3(8)-hydroxyethyl-8(3)-vinyldeuteroporphyrin (HVD or VHD) formed as a result of conversion of one of the hydroxyethyl groups of HP into a vinyl group through a dehydration reaction; and this particular compound is superior to HP in the carcinolytic effect by irradiation of laser in culture cell.

However, the above method cannot determine at which one of the hydroxyethyl groups the dehydration reaction has taken place, namely, whether the dehydration reaction has occurred at the 3rd position or 8th position. In other words, it cannot determine whether the reaction product is HVD or VHD. Furthermore, the raw material HP cannot by itself be obtained in any pure form. These drawbacks have raised substantial obstacles in developing it as a photosensitizer which is suitable for use in the laser irradiation therapy of cancers.

With the foregoing in view, the present inventor has carried out an extensive research to overcome such drawbacks. As a result, it has been found that the novel compounds represented by the general formula (I) may be obtained in their pure forms by subjecting their corresponding salts or alkyl esters of protoporphyrin, which is produced in a large volume as a hypohepatia curing agent and is readily available, to alcoholysis and these novel compounds have excellent photosensitizing effects, leading to completion of this invention.

In one aspect of this invention, there is thus provided a deuteroporphyrin derivative represented by the following general formula (I):

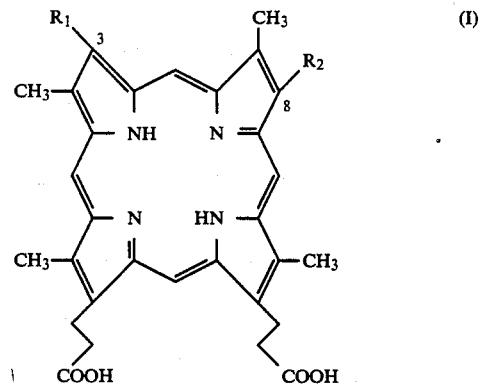

wherein one of $R_1$ and $R_2$ means —CH(CH$_3$)—OR, R being a lower alkyl group, and the other denotes —CH=CH$_2$, or $R_1$ and $R_2$ both mean —CH(CH$_3$)—OR, R having the same meaning as defined above, or a salt thereof.

The deuteroporphyrin derivatives (I) and their salts can be readily obtained in pure forms and are useful as photosensitizers in the laser irradiation therapy of cancers.

The above and other objects, features and advantages of this invention will become apparent from the following description and appended claims, taken in conjunction with the accompanying sole drawing, in which:

FIG. 1 is a high-speed liquid chromatogram of a dichloroethane extract of reaction products obtained by subjecting protoporphyrin dimethyl ester to alcoholysis.

The deuteroporphyrin derivatives of this invention can be produced by treating their corresponding salts or alkyl esters of protoporphyrin with an acid in an alcohol so as to subject the salts or alkyl esters to alcoholysis and in the case of the esters, followed by de-esterification.

Hydrogen chloride or the like may be used as the acid. The reaction may be conducted by boiling the reaction mixture for several hours. In this manner, the reaction product will be a mixture of a 3-alkoxyethyl-8-vinyl-deuteroporphyrin formed by the alcoholysis of the vinyl group at the 3rd position, 3-vinyl-8-alkoxyethyl-deuteroporphyrin obtained by the alcoholysis of the vinyl group at the 8th position, and 3-alkoxyethyl-8-alkoxyethyl-deuteroporphyrin formed by the alcoholysis of both vinyl groups. They can however be readily separated from one another by making use of differences among their properties. For example, a reaction product obtained by subjecting protoporphyrin dimethyl ester to methanolysis with hydrogen chloride in methanol may be subjected to chromatography in a silica gel column. By eluting the silica gel column, the raw material, protoporphyrin dimethyl ester is first eluted, followed by 3-methoxyethyl-8-vinyl-deuteroporphyrin (MVD) dimethyl ester, 3-vinyl-8-methoxyethyl-deuteroporphyrin (VMD) dimethyl ester and then 3-methoxyethyl-8-methoxyethyl-deuteroporphyrin (MMD) dimethyl ester. Thus, these esters can be isolated from one another. Upon hydrolysis of these dimethyl esters, their corresponding deuteroporphyrin derivatives of the formula (I) can be obtained.

The invention will next be described by the following examples.

EXAMPLE 1

(i) Suspended in 500 ml of methanol was 1 g of protoporphyrin dimethyl ester, to which hydrogen chloride gas was introduced until saturation. The thus-saturated suspension was boiled for 3 hours. It was then poured into 1 liter of a 10% aqueous solution of ammonium carbonate, followed by extraction of the resultant mixture with 200 ml of dichloroethane. After washing the extract with water, the extract was dried over sodium sulfate. The extract was then poured into a silica gel column which had in advance been washed with dichloroethane, thereby causing the silica gel column to adsorb the components of the reaction mixture thereon. The silica gel column was thereafter eluted with dichloroethane. First of all, the raw material, protoporphyrin dimethyl ester was eluted.

(ii) A fraction which was eluted second (which was confirmed to form a single spot by TLC) was collected. The solvent was distilled of and the residue was recrystallized from toluene, thereby obtaining 0.13 g of MVD dimethyl ester (yield: 13%).

Elemental analysis. Calculated for $C_{37}H_{42}N_4O_6$: C, 71.36; H, 6.80; N, 9.00. Found: C, 71.31; H, 6.93; N, 9.02.

Mass: Calculated.: 622. Found: 623 (M+1).

NMR (400 MHz, in $CDCl_3$) ppm: 10.54 (1H, s, 5-CH), 10.08 (1H, s, 10-CH), 10.06 (1H, s, 20-CH), 9.92 (1H, s, 15-CH), 8.27, 8.24, 8.23, 8.20 (1H, d, $8^1$-CH), 6.36, 6.31 (1H, d, $8^2$-$CH_2$), 6.16, 6.15 (1H, d, $8^2$-$CH_2$), 6.13, 6.12, 6.06, 6.04 (1H, q, $3^1$-CH), 4.34, 4.32, 4.30, 4.28 (4H, q, $13^1$, $17^1$-$CH_2$—) 3.72 (3H, s, 7-$CH_3$), 3.69 (3H, s, 2-$CH_3$), 3.63 (6H, s, $13^3$, $17^3$ ester-$OCH_3$), 3.60 (3H, s, $3^1$-$OCH_3$)], 3.57 (3H, s, 12-$CH_3$), 3.52 (3H, s, 18-$CH_3$), 3.23, 3.22, 3.21, 3.20 (4H, q, $13^2$, $17^2$-$CH_2$—) 2.27, 2.25 (3H, d, $3^2$-$CH_3$), −3.76 (2H, s, N-H).

(iii) A fraction which was eluted third (which was confirmed to form a single spot by TLC) was collected. The solvent was distilled off and the residue was recrystallized from methanol, thereby obtaining 0.10 g of VMD dimethyl ester (yield: 10%).

Elemental analysis: Calculated for $C_{37}H_{42}N_4O_5$: C, 71.36; H, 6.80; N, 9.00. Found: C, 71.35; H, 6.95; N, 8.67.

Mass: Calculated: 622. Found: 622.

NMR (400 MHz, in $CDCl_3$) ppm: 10.48 (1h, s, 5-CH), 10.18 (1H, s, 10-CH), 9.95 (1H, s, 20-CH), 9.88 (1H, s, 15-CH), 8.23, 8.20, 8.19, 8.16 (1H, d, $3^1$-CH), 6.32, 6.32, 6.28, 6.27 (1H, d, $3^2$-$CH_2$—), 6.14, 6.13, 6.11, 6.11 (1H, d, $3^2$-$CH_2$—), 6.07, 6.06, 6.04, 6.03 (1H, q, $8^1$-CH—), 4.39, 4.37, 4.35 (2H, t, $13^1$-$CH_2$—), 4.32, 4.30, 4.28 (2H, t, $17^1$-$CH_2$—), 3.69 (3H, s, 7-$CH_3$), 3.66 (3H, s, 2-$CH_3$), 3.63 (6H, s, $13^3$, $17^3$ eser-$OCH_3$), 3.61 (3H, s, $8^1$-$OCH_3$), 3.55 (3H, s, 12-$CH_3$), 3.48 (3H, s, 18-$CH_3$), 3.28, 3.26, 3.24, 3.22, 3.20 (4H, t, $13^2$, $17^2$-) 2.27, 2.25 (3H, d, $8^2$-$CH_3$), −3.78 (2H, s, N-H).

(iv) A fraction which was eluted forth (which was confirmed to form a single spot by TLC) was collected. The solvent was distilled off to obtain 0.08 g of MMD dimethyl ester (yield: 8%).

Mass: Calculated: 654. Found: 655 (M+1).

NMR (400 MHz, in $CDCl_3$) ppm: 10.55 (1H, s, 5-CH), 10.51 (1H, s, 10-CH), 10.10 (1H, s, 20-CH), 10.05 (1H, s, 15-CH), 6.07, 6.05, 6.04, 6.02 (2H, q, $3^1$-, $8^1$-CH), 4.42, 4.40, 4.39, 4.39 (4H, q, $13^1$-$17^1$-$CH_2$), 3.71 (3H, s, 7-$CH_3$), 3.70 (3H, s, 2-$CH_3$), 3.66 (6H, s, $13^3$-, $17^3$-ester-$OCH_3$), 3.63 (6H, s, $3^1$-$8^1$-$OCH_3$), 3.62 (3H, s, 12-$CH_3$) 3.61 (3H, s, 18-$CH_3$), 3.31, 3.30, 3.29, 3.28, 3.27, 3.26 (4H, t, $13^2$, $17^2$-$CH_2$—), 2.27, 2.25 (6H, d, $3^1$-$8^1$—$CH_3$), −3.69 (2H, s, N-H).

(v) The extract obtained in the above Step (i) was subjected to high-speed liquid chromatography [column: μ-bond pack C-18 (Nippon Waters Corporation), eluting solvent: methanol, detection: 400 nm absorbance]. Results are shown in FIG. 1. Furthermore, the thus-isolated components were each identified by high-speed chromatography. As a result, these components were 24.9% of MMD dimethyl ester (elution time: 2.3 minutes), 50.7% of MVD dimethyl ester and VMD dimethyl ester (3.4 minutes), and 24.3% of the raw material (5.6 minutes) respectively.

EXAMPLE 2

One gram of each of the MVD dimethyl ester, VMD dimethyl ester and MMD dimethyl ester, all of which were obtained in Example 1 Steps (ii)–(iv), was taken up in 50 ml of pyridine, followed by an addition of 20 mg of sodium hydroxide in methanol. The resultant mixture was stirred at 90° C. for 2 hours. After the reaction, the resultant crystalline precipitate was collected by filtration and was then dried. Disodium MVD, disodium VMD and disodium MMD were each obtained in an amount of 0.1 g.

EXAMPLE 3

The cultured cell strain JTC-16 originated from DAB-induced rat hepatoma (AH-7974) were cultured at 37° C. on a DM-170 culture medium. In the middle of the logarithmic phase, disodium MVD, disodium VMD or disodium MMD was added in an amount of 5 μg/ml. After incubating the cells for 24 hours, argon laser having a wavelength of 630 nm was irradiated at an energy level of 5 mW/cm². Results are summarized in Table 1.

TABLE 1

|  | 1 min. | 3 min. | Dark place |
|---|---|---|---|
| Disodium MVD | ++ | +++ | − |
| Disodium VMD | − | ++ | − |
| Disodium MMD | − | + | − |
| HPD | + | ++ | − |
| HP | − | + | − |
| Control | − | − | − |

(Note)
+++ Cells in ghost formation and fragmentation.
++ Cell in smooth surface.
+ Cells in vacuolization.
− Cells in normal state.

As shown in Table 1, no changes were observed on the control cells during the 3-minute irradiation of laser. However, disodium MVD developed the reactions faster than HPD. In the case of disodium VMD, it took substantially the same time as HPD for the reactions. On the other hand, disodium MMD required approximately the same same time as HP for the reactions.

Having now fully described the invention, it will be apparent to one of ordinary skill in the art that many changes and modifications can be made thereto without departing from the spirit or scope of the invention as set forth herein.

I claim:

1. A deuteroporphyrin derivative represented by the following formula:

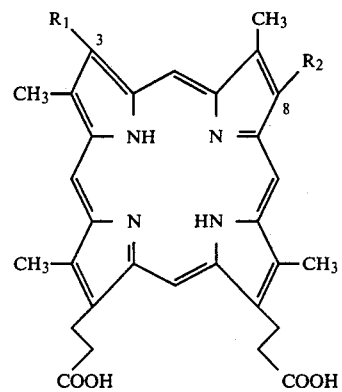

wherein one of $R_1$ and $R_2$ is $-CH(CH_3)-OR$, wherein R is a lower alkyl group, and the other $R_1$ or $R_2$ substituent is $-CH=CH_2$, or a photosensitively active salt thereof.

2. A deuteroporphyrin derivative according to claim 1, which is a 3-alkoxyethyl-8-vinyl-deuteroporphyrin or a photosensitively active salt thereof.

3. A deuteroporphyrin derivative according to claim 1, which is a 3-vinyl-8-alkoxyethyl-deuteroporphyrin or a photosensitively active salt thereof.

* * * * *